United States Patent [19]
Hounsfield

[11] 3,946,234
[45] Mar. 23, 1976

[54] APPARATUS FOR EXAMINING BODIES BY MEANS OF PENETRATING RADIATION

[75] Inventor: Godfrey Newbold Hounsfield, Newark, England

[73] Assignee: E M I Limited, Hayes, England

[22] Filed: Aug. 30, 1974

[21] Appl. No.: 502,080

[30] Foreign Application Priority Data
Aug. 31, 1973 United Kingdom............... 41191/73
Feb. 2, 1974 United Kingdom................ 4928/74

[52] U.S. Cl........................... 250/363 S; 250/445 T
[51] Int. Cl.²........................................... G01T 1/20
[58] Field of Search........... 250/358, 359, 360, 362, 250/363, 366, 367, 369, 393, 394, 395, 445 T, 363 S

[56] References Cited
UNITED STATES PATENTS
3,778,614  12/1973  Hounsfield........................ 250/362

*Primary Examiner*—Davis L. Willis
*Attorney, Agent, or Firm*—Fleit & Jacobson

[57] ABSTRACT

An apparatus is disclosed for examining a body by means of penetrating radiation in which the radiation is provided in the form of a sector subtending a predetermined angle at the radiation source and detected by an array of detectors in the plane of the sector. The source and detectors are scanned laterally in the plane of the sector and orbited about an axis perpendicular to that plane at an angular rate which takes account of the angle subtended by the sector. Output signals produced by the detectors related to radiation incident at different angles in the sector during the scanning movements, are used to construct a distribution of absorption coefficients for a planar slice of the body.

9 Claims, 5 Drawing Figures

APPARATUS FOR EXAMINING BODIES BY MEANS OF PENETRATING RADIATION

This invention relates to apparatus for examining a body by means of penetrating radiation such as X- or γ- radiation.

One example of such apparatus is described in U.S. Pat. No. 3,778,614 and according to this example, the apparatus comprises a scanning frame in which are mounted a source of radiation, say X-rays, and detecting means which face each other across an aperture in which the body of a patient can be located. The source of radiation and the detecting means are mounted for lateral scanning so the beam of radiation, to which the detecting means is sensitive, scans laterally across a planar section of the body, which it is desired to examine. Moreover, the scanning frame can be orbited in discrete small angular steps. As a consequence, output signals can be derived from the detecting means representing the transmission or absorption of the section of the body to the radiation from the source along a number of closely spaced parallel beam paths, one set of such paths being derived after each angular step of the orbital motion. From the many sets of output signals thus obtained a representation of a variable transmission or absorption of the plane section of the body under examination, is reconstructed.

With apparatus such as described in the aforesaid patent specification, the time occupied by the scanning is relatively long since the transverse scanning has to be sufficiently slow to allow an adequate photon count to be obtained for each of the closely spaced parallel beam paths. This renders the results obtained from parts of the patient's body liable to be obscured by movement of the patient's organs.

It is an object of this invention to reduce this disadvantage.

According to the invention there is provided apparatus for examining a body by means of penetrating radiation, such as X- or γ- radiation, including source means for irradiating the body with said radiation, detector means for detecting the radiation after passage through the body, means for orbiting the source and detector means around the body so as to irradiate a planar section of said body from a plurality of different directions and means for moving the source and detector means laterally in said plane so as to scan said radiation across said planar section, wherein said detector means includes a plurality of detectors for producing output signals respectively related to the radiation incident at different angles within a sector of radiation emanating from said source, wherein linking means links said source means to said detector means to substantially prevent relative movement between said detectors and said sector of radiation, and wherein said orbiting means moves the said source and detector means at an angular rate which takes account of the angle subtended by said sector.

In order that the invention may be clearly understood and readily carried into effect one example of the invention will now be described with reference to the accompanying drawings in which.

Figure 1:
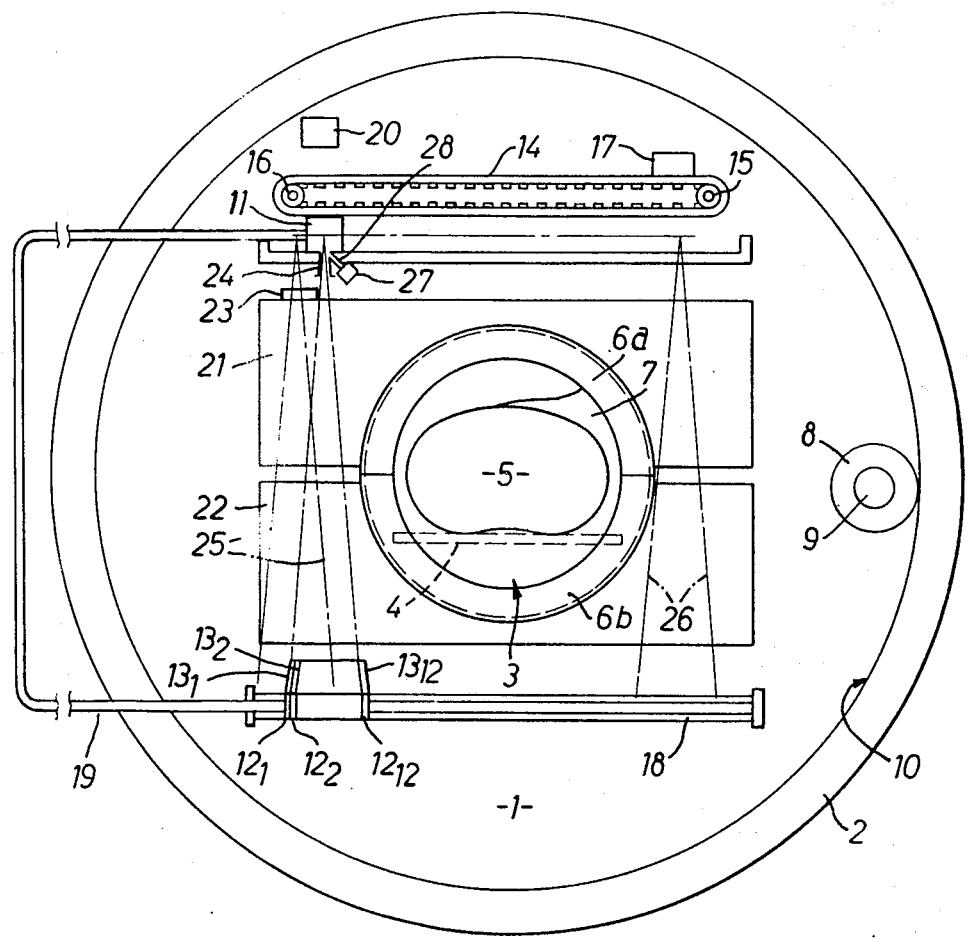
FIG. 1 illustrates diagrammatically the scanning mechanism of the example.

Referring to the drawings, the apparatus comprises a rotary member which is rotatable inside a fixed casing member 2. The rotary member 1 has a central aperture 3 in which the body of the patient to be examined can be inserted, lying for example on a support 4. The body of a patient is represented in section by the outline 5. A retaining means in the form of a two piece collar 6a, 6b is provided for locating the patient, a water bag 7 or other absorbent material being inserted between the collar and the patient to avoid an air gap.

A toothed gear wheel 8, driven by a motor 9, is provided for driving the rotatable member 1 so as to produce orbital scanning of the patient around the axis of the rotatable member 1. The gear wheel 8 engages teeth formed round the inner periphery 10 of the casing member 2. The rotatable member carries a source 11 of penetrating radiation, X-radiation in this example, and facing the source 11 a bank of detectors $12_1$, $12_2$, .... $12_n$. Each detector, which comprises a scintillator and a photomultiplier, has its own collimator, $13_1$, $13_2$, ... $13_n$ respectively. The source of radiation is arranged to be an effective point source and it has a collimator 24 which confines the emergent radiation to a 10° sector in a plane section normal to the axis of the rotary member 1. The collimators 13 are inclined as shown, subtending a total angle of 10° at the point source of the radiation. There may be for example 30 detectors in the bank 12, and a corresponding number of collimators 13 inclined to each other at an angle of ⅓°. In order to accommodate the detectors in a relatively confined space the pattern disclosed in our U.S. application Ser. No. 493,403 dated July 31, 1974 (British Pat. No. 39145/73) may be adopted.

The source 11 is secured to a toothed belt 14 driven by a toothed drive shaft 15 journalled in the rotatable number 1, the belt being extended between the shaft 15 and a second undriven shaft 16 also journalled in 1. The shaft 15 is driven by a reversible motor (not shown) the controls of which are interlocked with those of the motor 9. Since the source 6 is massive, a counter balance weight 17 is provided, also secured to the belt 14 so as to move reciprocably with the source. The detector 12 and collimators 13 are movable in fixed guides secured to the rotatable member, the guides being parallel to the longitudinal runs of the belt, and the source 11 is also provided with supporting guides. The detectors 12 and collimators 13 are moreover linked to the source 11 by a yoke 19. In operation of the apparatus the belt 14 is driven to and fro by the reversible motor which drives the shaft 15 to cause the radiation from the source 11 to execute successive lateral tranverses in a plane section of the patient's body. The detectors and collimators follow this scanning movement, since they are linked to the source 11 by yoke 19, so that output signals are derived during any one lateral scan from the 30 detectors, representing the transmission or absorption along 30 parallel sets of beam paths in the planar section under examination.

In the lateral scanning arrangement, referred to in relation to the aforementioned United States Patent, employing a single detector an orbital movement of the angle between adjacent sets of beams is produced between each lateral scan of the source and detector. This is repeated until the source and detector have moved through, for example, 180°. By using 30 detectors, in accordance with this example of the invention, sets of beams are produced such as would have been provided by 30 orbital movements; in this example of one third of a degree each because the detectors are so inclined. Thus the lateral scan need only be repeated at 10° intervals. This movement is therefore caused to occur by the motor 9 before the next lateral scan provides a further 30 sets of output signals, this scan being in a reverse sense to the previous one. A photo cell device represented diagrammatically by the block 20, is provided to monitor the lateral scanning displacements. It will therefore be seen that a full 180° orbital scan can be effected after only 18 orbital steps instead of the 540 which would be required to produce parallel sets of beams at ⅓° spacing, using only a single detector. The speed of scanning can therefore be relatively fast. If desired a further 180° scan can be effected, after a sideways step of the detectors 12 and collimator 13, as described in U.S. application Ser. No. 489,084. Alternatively such a sideways step can be provided between each lateral scan and the orbital step only provided after two such scans. Thus two, displaced, lateral scans would be provided for each orbital position. If one of these expedients is adopted, the number of detectors 12 and collimators 13 may be reduced, the angle between adjacent collimators being doubled.

The use of a plural number of detectors does however give rise to another problem. The detector usually comprises a scintillator which is exposed to photons transmitted along the beam path to which the detector is sensitive. The scintillator converts the X-ray or γ-ray photons into visible light impulses, and the detector also includes a photomultiplier tube for producing an output signal indicative of the numbers of photons impinging on the scintillator. However, it has been found in practice that the sensitivity of a detector is liable to drift during the time required for scanning. In addition, if more than one detector is used, differential drift can occur. These effects which can give rise to significant spurious signals, may be mitigated by means to be described hereinafter.

As represented in FIG. 1 two attenuating blocks 21 and 22 are fitted round the patient's collar 6a, 6b. These blocks may be made of perspex which has an absorption coefficient for X-rays similar to that of body tissue. The blocks are cut as shown to fit round the collar, but as they are secured to the rotating member 1, they must turn freely round the collar. They are held in position by suitable means not shown. It should be noted that the collar need not be exactly central provided the blocks can rotate properly about it. The blocks also extend laterally as indicated to allow monitoring to take place. A lead block 23 is positioned above the prespex block 21 near one side so that the segment of X-rays emerging from the collimators 24 when the source 11 is near one extremity of its travel is intercepted by the lead block. Moreover, after the sector of X-rays leaves the area bounded by the patient's collar 6a, 6b and before it reaches the lead block 23, it passes for a time through the attenuating blocks 21 and 22 without other obstruction. Similarly, when the source 11 is near the other extremity of its travel the sector of X-rays passes only through the blocks 21 and 22. The chain dotted lines 25 and 26 respectively indicate the sector of X-rays at the left hand extremity of its travel and near the right hand extremity of its travel. A reference detector 27 is mounted close to the source of X-rays 11 so that it receives radiation through a collimator 28. The detector 27 is provided to monitor the energy of the X-ray source 11.

Figure 2:
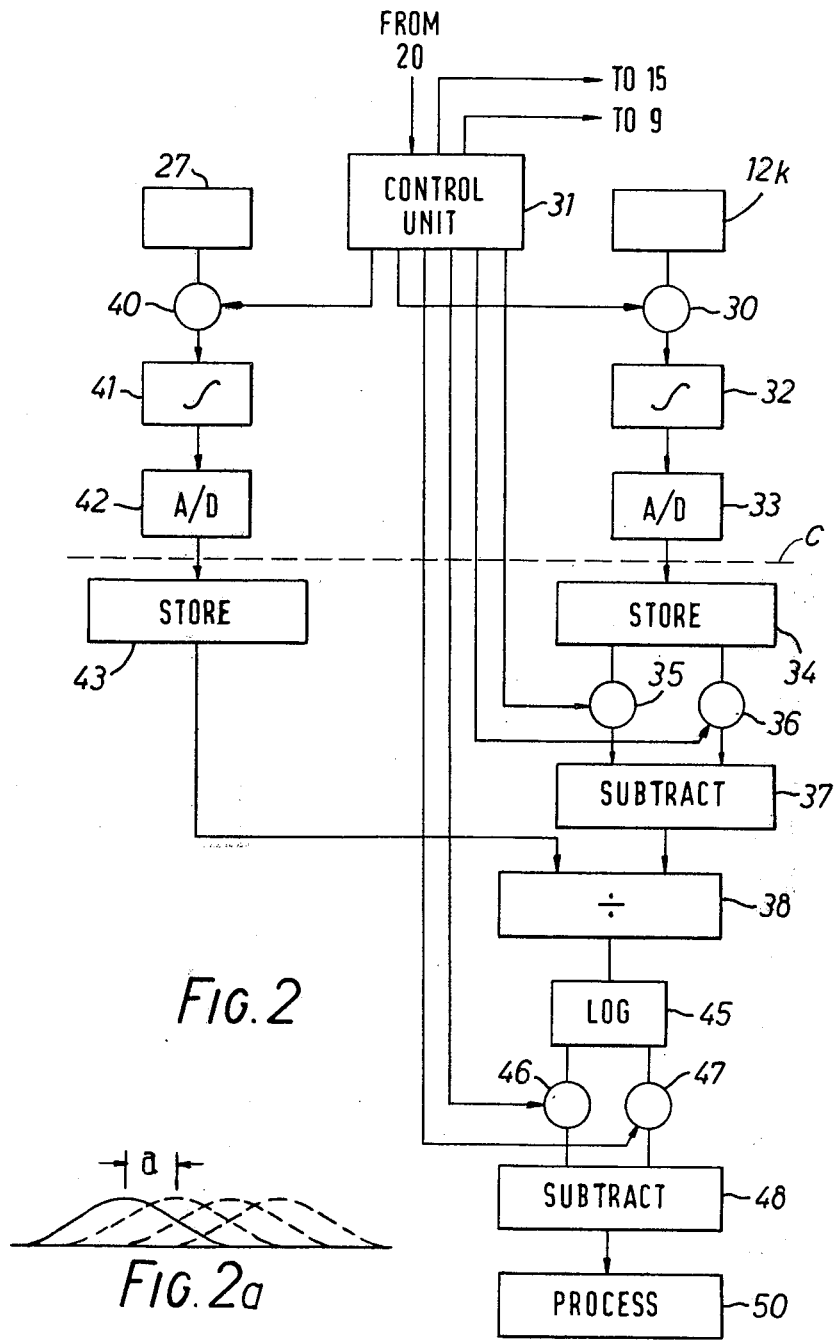
FIG. 2 is a diagrammatic representation of the circuit for manipulating the output signals.

FIG. 2 is a block diagram illustrating the processing circuits for use with the scanning apparatus shown in FIG. 1. In FIG. 2 reference 27 indicates the reference detector while reference $12_k$ indicates any one of the detectors in the bank $12_1, ... 12_n$. The output signal of detector $12_k$ is applied to a gate 30 which is opened at predetermined times by sampling pulses from a master control circuit 31. This master control circuit receives inputs from, inter alia, the photocell device 20 and feeds out suitable control signals to the reversing motor for the shaft 15 and to the motor 9. The sampling pulses which it feeds to the gate 30 and the corresponding gates for the other detectors of the block 12 are so timed as to cause each detector to feed out a succession of output signals corresponding to the transmission of a set of parallel beam paths. The orientation of the set of paths for the particular detector $12_k$ is determined by the respective collimater $13_k$ and, of course by the particular angular setting of the rotatable member 1. During each sampling interval, the output of the detector $12_k$ is integrated in an integrator 32 and then converted to digital code form in an analogue to digital converter 33. The signal generated during each sampling pulse is stored in its digital form in a store 34. The sector of X-rays is intercepted by the lead 23 only during alternate lateral traverses of the source 11, and therefore the corresponding output signal from each detector 12 is stored for the duration of two traverses. The signals of a particular parallel set in the store 34 include those obtained when the sector of X-rays was last intercepted by the block 23, those obtained in the particular traverse when the sector passed through the attenuating blocks 21 and 22 without other obstruction, and those obtained when passing through the zone bounded by the patient's collar. Gate 35 is provided for selecting the output signal derived from the detector $12_k$ at the time when the X-rays were intercepted by the lead. Another gate 36 is provided for selecting the signals generated at other times during a particular traverse by the detector $12_k$. The selection is controlled by sampling pulses provided by the master control circuit 31 and the operation is such that whereas successive signals are selected by the gate 36 the "lead" signals are selected repetitively by the gate 35 at each sampling time. There are, therefore, two signals at each sampling time of the gates 35 and 36, and these two signals are applied to a digital subtracting circuit 37. This circuit is arranged to subtract the "lead" signals from the other signals so that after subtraction the other signals represent the transmission or absorption of the respective beam paths to the extent that they differ from that of the lead block 23. In this way the effect of "dark current" or "lag" in the detectors 12 is largely removed. The resultant signals are then fed to a dividing circuit 38.

The reference detector 27, previously referred to, has an output gate 40, which receives sampling pulses from the master control circuit 31, coincident with the sampling pulses applied to the gate 30. Signals passing through the gate 40 are integrated in an integrator 41 and converted to a digital form in a converter 42, these components corresponding to the integrator 32 and converter 33. The digitised reference signals from the detector 27 are then passed to a store 43 and stored for the duration of the ensuing lateral scan. The signals in the store 43 are fed, under the control of a gate if desired to the aforesaid dividing circuit 38. In the dividing circuit each signal from the detector $12_k$ is divided by the corresponding signal from the store 43 to compensate for variations in the energy of the source 11. The signals so compensated are passed to a log converting circuit 45 which translates each of the signals from the detector $12_k$ into its logarithm. The log signals are applied to two gates 46 and 47 which are controlled by pulses from the master control circuit 31. The gate 46 is opened when the sector of X-rays is passing through the area bounded by the patient's collar during any particular lateral traverse while the gate 47 is open when the X-rays are passing, without other obstruction through the blocks 21 and 22 at the beginning of the same traverse. The outputs of gate 46 may therefore be termed the "picture" signals while that of the gate 47 may be termed the "reference" signal. The reference signal, in the case considered for the detector $12_k$, is read out repeatedly to coincide with each picture signal and it is subtracted from the picture signal so as to reference the latter to the transmission or absorption of perspex. It should be noted that it is not essential to reference the picture signals to the transmission of perspex as described provided some degradation of the picture is acceptable. If this step is omitted the circuit of FIG. 2 may be simplified and the size of the perspex blocks may be reduced by the extent of the lateral extension required for the monitoring. As a further development they may be entirely omitted providing other attenuating means are provided for equalising absorption across the scan.

In this example, however, the signals after referencing in this way are fed to a signal processor 50 to participate in the reconstruction of the variable transmissions or absorptions of the section under examination. This may be achieved as described in our aforesaid United States Patent or as described in our co-pending U.S. application Ser. No. 462,104. Of the components represented in FIG. 2 of the drawing those located below the line C may take the form of a digital computer which is appropriately programmed, and which feeds its output to a suitable picture reconstruction device. The collimators 13 in this example are each of width $2a$ in the plane of the sector of X-rays and the respective integrator 32 for each collimator is arranged to integrate for successive time intervals which equal approximately the time taken for the source 11 and detectors 12 to travel a distance $a$. This is the sampling interval in this example of the invention. The integration interval is less than $a$ only by the time necessary to read out and reset the integrator 32 between successive integrator periods. It can be shown that when the collimators are of width $2a$ and the integration for producing each output signal of a set is carried out over successive distances $a$ the output signals derived from the circuit of FIG. 2 are as if derived from sampling beams of the cross sectional intensity indicated in FIG. 2a. Each beam is approximately $4a$ wide and as shown overlaps the two adjacent beams on each side of it. The smoothing of the beam cross sectional intensity curve is attributable to factors including the fact that the radiation of the source 11 is not wholly uniform over the source aperture, but falls off from the centre. The beam intensity distribution approximates to a sinusoidal distribution and effectively band limits the output signals to a upper spatial frequency of $(1/2a)$, namely half the sampling frequency.

In U.S. Pat. application Ser. No. 476,300, alternative means are provided, for presenting substantially the same profile to the radiation for different scanning positions, and any of these alternatives may be used to replace "Perspex" blocks 21 and 22. Preferably the blocks may take the form shown in FIG. 3. Blocks 21 and 22 are replaced by four shaped attenuators such as 51. It should be noted that the attenuators 51 could be joined if required to form one upper and one lower attenuator each of a saddle shape. As has been explained in the aforementioned application Ser. No. 476,300 these attenuators do not need to be in contact with the patient's collar $6a$ and $6b$ nor even to surround it providing that they are correctly shaped to provide approximately the required correction to the beam paths for all beam dispositions. In some circumstances it may not be possible to render the absorption, when the body is replaced by a constant reference absorber, entirely constant across the lateral scan, as is intended. However the computer arranged to process the output signals is programmed to take into account any residual variations in absorption due to causes other than the body. In this example the attenuators 51 are formed of aluminium, carbon or other suitable material. It should be noted that the use of aluminium attenuators may introduce variations of frequency distribution, of the radiation used, in the course of a scan. In that case the processing computer must be further programmed to correct the edge values after log conversion by varying them in relation to the amount of aluminium in the beam from the edge to centre.

Figure 4:
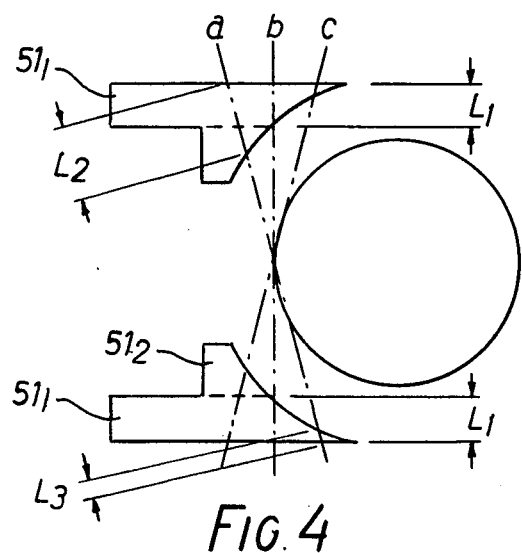
FIG. 4 illustrates in detail part of the arrangement of FIG. 3.

The shape of the preferred attenuators is shown more clearly in FIG. 4. If a scanning procedure employing a single beam of radiation were being used the attenuators should have the shape of section $51_1$ to one side of the broken line (i.e., ignoring the portions $51_2$). If this were the case, the single beam, which corresponds to the central beam $b$ in the sector of radiation actually used would be attenuated by a path of length $2L_1$, in the position shown, through the attenuators only. However since a sector of radiation is actually being used, as hereinbefore described, inclined beams such as $a$ and $c$ will traverse different path lengths through the attenuators. For this reason extensions such as $51_2$ are provided and shaped such that beam $a$ traverses lengths $L_2$ and $L_3$ through the upper and lower attenuators, where the sum of $L2$ and $L3$ is approximately equal to $2L_1$. This equality cannot be achieved exactly for all beams in all the periods required, but by this means it is possible to arrange that all beams pass through substantially the same attenuation path length.

Figure 3:
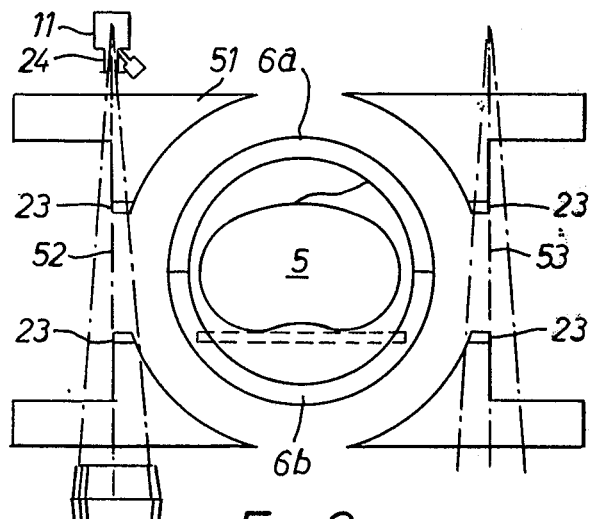
FIG. 3 illustrates diagrammatically a scanning mechanism showing a modification to the invention.

In relation to FIG. 1 an arrangement was described wherein the beams of radiation pass, at the ends of the scans, through a path entirely in the perspex blocks 21 and 22 to provide absorption recordings referenced to the absorption of perspex. In the arrangement described using metal attenuators the equivalent procedure is to pass the beams solely through the attenuators 51 together with the air gap between. However at the equivalent positions the attenuators 51 have been extended, as described, by extensions $51_2$ and would not provide the required path lengths for such referencing. In this example therefore the lead path has been provided as shown in FIG. 3 by four blocks of lead 23 at the extremes of the extensions. The attenuators are then continued beyond these positions with parallel sides to provide beam paths for the reference readings.

In this example of the invention to reduce the necessary size of the attenuators 51 the reference readings are taken in two parts at opposite ends of the linear scanning range. Referring to FIG. 3, those beams in the left half of the fan, i.e., to the left of line 52 are referenced to both lead and the attenuating material at the left hand and of the scanning range. Conversely those in the right half of the fan are referenced at the right hand end of the scanning range, i.e., to the right of line 53. The reference readings thus obtained are used not only for the scan following their being obtained but also for absorption readings, retained in a memory, for the previous scan. This may be important for the first scan for which there will be no prior reference values.

It will be appreciated that the signals for all the detectors 12 will be processed in the same way as described for the detector $12_k$. A number of modifications may be made to the example described. For example, instead of taking the reference readings, which are subtracted from the patient's reading in the circuit 48, through perspex, they may be taken through water enclosed in a suitable container or through some other medium. It will also be appreciated that the angles of the sector of the X-rays from the source 11 may differ for 10° and the number of detectors 12 and collimators 13 may also be varied. Even if the number is as small as two, appreciable advantage can be obtained.

Furthermore the water bag inserted between the patient and the two piece collar may be replaced by other means for avoiding an air gap. A suitable alternative would be a polystyrene or rubber foam impregnated with an absorbing material such as lead or molybdenum so that the foam provides the same absorption as water. Such foam may be conveniently wrapped round the patient before the collar is fitted.

The solid attenuating material outside the patients collar 6a and 6b may be replaced by a water reservoir as described for example in U.S. Pat. No. 3,778,614 or co-pending U.S. application Ser. No. 358,980.

I claim:

1. Apparatus for examining a body by means of penetrating radiation, such as X or γ radiation, including source means for irradiating the body with said radiation, detector means for detecting the radiation after passage through the body, means for orbiting the source and detector means around the body so as to irradiate a planar section of said body from a plurality of different directions and means for moving the source and detector means laterally in said plane so as to scan said radiation across said planar section, wherein said detector means includes a plurality of detectors for producing output signals respectively related to the radiation incident at different angles within a sector of radiation emanating from said source, wherein linking means links said source means to said detector means to substantially prevent relative movement between said detectors and said sector of radiation and wherein said orbiting means moves the said source and detector means at an angular rate which takes account of the angle subtended by said sector.

2. An apparatus according to claim 1 wherein said orbiting means moves said source and said detector means by approximately the angle subtended by said sector for each of said lateral scans.

3. Apparatus for examining a body by means of penetrating radiation, such as X- or γ- radiation, including source means for producing radiation within a planar sector with the radiation travelling along radii within said sector effectively from a point source, retaining means having an aperture in which the body to be examined can be located, detector means including a plurality of detector elements for detecting the radiation transmitted through said body along respective radial beam paths included in said sector, scanning means for repetitively concomitantly scanning said source means and said detector means laterally in said plane so that said radiation scans across a planar section in said body and output signals are derived from each detector element corresponding to a respective parallel set of rays passing through said section, and orbiting means for orbiting said source means and said detector means around said body so that said planar section is irradiated by said radiation from a plurality of different directions, said orbiting means moving said source means and said detector means through an angle approximating the angle subtended by said sector for each successive said lateral scan.

4. An apparatus according to claim 3 wherein said orbiting means moves said source and said detector means in steps between said lateral scans.

5. An apparatus according to claim 3 wherein said radiation passes through compensating attenuating material in addition to said body and said retaining means, said attenuating material being arranged so that said radiation suffers substantially the same absorption for any dimension of said body and of said retaining means in said plane, assuming the body to be of uniform absorption in said plane, said attenuating material being so shaped that the radiation transmitted along each of said beams is substantially equivalently compensated despite differences of angle within the sector.

6. An apparatus according to claim 5 wherein said radiation passes through said attenuating material, without passing through said body or said retaining means, to provide absorption data relating substantially only to said attenuating material at predetermined points in said lateral scans, and said last mentioned data are used as reference values for the absorption data obtained from the preceding lateral scan, the absorption data relating to said attenuating material being obtained at one end of each lateral scan for the radiation in part of said sector and at the other end of each lateral scan for the radiation in the rest of said sector.

7. An apparatus according to claim 5 wherein said attenuating material is aluminium.

8. Apparatus according to claim 3 in which said scanning means produces alternate scans in opposing directions.

9. Apparatus for examining a body by means of penetrating radiation such as X- or γ- radiation, including source and scanning means for producing radiation within a planar sector with the radiation travelling along radii within the sector effectively from a point source, retaining means having an aperture in which the body to be examined can be located, said source and scanning means including means for displacing said effective point source of radiation so as to cause said sector to repetitively scan laterally in said plane so that said radiation scans across a planar section in said body, detector means including a plurality of detector elements for detecting radiation transmitted through said body along radial beams included in said sector, said detector means providing output signals relating to the transmission of said radiation along said beam during said scans, and orbiting means for orbiting said source and detector means around the body so that said planar section of said body is irradiated by said radiation from a plurality of different directions, and wherein said orbiting means moves said source and detector means through an angle approximating the angle subtended by said sector for each successive said lateral scan.

* * * * *